US012806392B2

(12) United States Patent
Bertollo

(10) Patent No.: US 12,806,392 B2
(45) Date of Patent: Nov. 24, 2026

(54) MICRONEEDLE ARRAYS

(71) Applicant: Latch Medical Limited, Dublin (IE)

(72) Inventor: Nicky Bertollo, Dublin (IE)

(73) Assignee: Latch Medical Limited, Dublin (IE)

( * ) Notice: Subject to any disclaimer, the term of this patent is extended or adjusted under 35 U.S.C. 154(b) by 348 days.

(21) Appl. No.: 18/572,242

(22) PCT Filed: Jun. 20, 2022

(86) PCT No.: PCT/EP2022/066748
§ 371 (c)(1),
(2) Date: Dec. 20, 2023

(87) PCT Pub. No.: WO2022/268731
PCT Pub. Date: Dec. 29, 2022

(65) Prior Publication Data

US 2024/0299718 A1 Sep. 12, 2024

(30) Foreign Application Priority Data

Jun. 21, 2021 (EP) .................................... 21180577

(51) Int. Cl.
*A61M 37/00* (2006.01)

(52) U.S. Cl.
CPC . *A61M 37/0015* (2013.01); *A61M 2037/0023* (2013.01); *A61M 2037/0053* (2013.01)

(58) Field of Classification Search
CPC .. A61M 2037/0046; A61M 2037/0053; A61M 37/0015; A61M 2037/0023; A61M 2037/0061
See application file for complete search history.

(56) References Cited

U.S. PATENT DOCUMENTS

2003/0199810 A1* 10/2003 Trautman ................ B81B 1/008 264/293
2007/0293816 A1* 12/2007 Chan ................. A61M 37/0015 604/46
2016/0220802 A1* 8/2016 Huang .............. A61M 37/0015
2019/0314012 A1* 10/2019 Bertollo ............... A61B 17/064

FOREIGN PATENT DOCUMENTS

CN 112617749 A 4/2021
WO 2007127815 A2 11/2007
WO 2018069543 A1 4/2018

OTHER PUBLICATIONS

International Search Report and Written Opinion dated Sep. 2, 2022, for corresponding International Application No. PCT/EP2022/066748 International Filing Date: Jun. 20, 2022 consisting of 11-pages.

* cited by examiner

*Primary Examiner* — Courtney Fredrickson
(74) *Attorney, Agent, or Firm* — Leech Tishman Fuscaldo & Lampl LLC

(57) ABSTRACT

The invention discloses a microneedle system comprising cooperating arrays of microneedles (12, 16) having particular geometries and orientations, and a method of manufacturing such a microneedle system which provides improved efficacy to the deployment and operation of devices employing the microneedle arrays manufactured according to the invention.

25 Claims, 6 Drawing Sheets

MICRONEEDLE ARRAYS

CROSS-REFERENCE TO RELATED APPLICATIONS

This application is a Submission under 35 U.S.C. § 371 for U.S. National Stage Patent Application of, and claims priority to, International Application Number PCT/EP2022/066748, entitled MICRONEEDLE ARRAYS, filed Jun. 20, 2022, which is related to and claims priority to European Patent Number 21180577.5, filed Jun. 21, 2021, the entirety of all of which are incorporated herein by reference.

FIELD OF THE INVENTION

The present invention relates to a microneedle system comprising cooperating arrays of microneedles and to a method of manufacturing such a microneedle system, the method of manufacture providing improved efficacy to the deployment and operation of medical devices employing microneedle arrays manufactured according to the invention.

BACKGROUND OF THE INVENTION

Microneedles are gaining increased use in various medical applications in view of the many documented benefits for both patients and medical professionals, for example reduced tissue trauma, surgery times and patient recovery, reduced risk of infection, and minimising the surgical or medical equipment needed in procedures involving microneedle based devices. Such microneedle based devices are also being used in applications in which the end user can apply and remove the device without requiring the intervention of a medical professional, for example in various drug delivery applications, for example large scale vaccination programmes.

International patent applications WO2018/069543 and WO2019/201903 provide detailed disclosures of the configuration and operation of microneedles and opposing microneedle arrays which may be provided in the form of a device or patch for application to a tissue substrate for various surgical and therapeutic uses, one particular use being drug delivery directly from or through the microneedles provided, which again may be used for delivering vaccinations or the like. The disclosures of WO2018/069543 and WO2019/201903 are incorporated herein in their entirety.

As a result of the increased use of microneedles in medical applications there is a growing need for large scale and economic methods of manufacturing microneedle arrays for use in such medical devices.

It is therefore an object of the present invention to provide a microneedle system which is operable to quickly and easily deploy microneedles into a tissue substrate such as the skin, and a method of manufacturing such microneedle arrays which provides for improved performance in the end product in addition to improved economy of manufacture.

SUMMARY OF THE INVENTION

According to a first aspect of the present invention there is provided a microneedle system for application to tissue comprising a first array of microneedles formed from and folded out of the plane of a first sheet; a second array of microneedles formed from and folded out of the plane of a second sheet; the first and second sheets overly one another and the second array of microneedles extends through an array of openings in the first sheet to be interspersed with the first array of microneedles; wherein the first array of microneedles is displaceable relative to the second array of microneedles in a direction parallel to the plane of the first and second sheets; characterised in that at least some of the microneedles are folded out of the plane of the first or second sheet about a fold axis that extends parallel to the direction of relative displacement between the first and second arrays of microneedles.

Preferably, the fold axis lies in the plane of the first or second sheet.

Preferably, the openings in the first sheet are shaped and dimensioned to facilitate the relative movement between the first and second arrays of microneedles.

Preferably, the openings in the first sheet are at least partially formed by folding a respective microneedle out of the first sheet to at least partially define the opening.

Preferably, a longitudinal axis of each of the microneedles in the first and second arrays extend at an oblique angle to the plane of the first or second sheet.

Preferably, a longitudinal axis of each of the microneedles of the first array extend in a first direction and a longitudinal axis of each of the microneedles of the second array extend in a second direction.

Preferably, the first direction extends away from the second direction.

Preferably, the longitudinal axis of each of the microneedles of the first array extend at a first oblique angle to the plane of the first and second sheet and the longitudinal axis of each of the microneedles of the second array extend at a second oblique angle to the plane of the first and second sheet.

Preferably, each of the microneedles of the first and second arrays comprises a tapered tip.

Preferably, the tip is tapered in multiple directions.

Preferably, the tip is multifaceted.

Preferably, each of the microneedles of the first and second arrays are substantially planar and lie in a plane perpendicular to the plane of the first and second sheet and parallel to the direction of relative displacement between the first and second sheets.

Preferably, the first and second sheets comprise metal.

Preferably, at least a part of one or more of the microneedles comprise an exterior coating.

Preferably, the coating comprises a pharmacologically active component.

Preferably, the first sheet is electrically isolated from the second sheet.

According to a second aspect of the present invention there is provided a method of manufacturing a microneedle system comprising the steps of forming a first array of microneedles in a first sheet; folding the first microneedles out of the plane of the first sheet; forming a second array of microneedles in a second sheet; folding the second microneedles out of the plane of the second sheet; overlying the first and second sheets such that the second array of microneedles extends through an array of openings in the first sheet to be interspersed with and displaceable relative to the first array of microneedles in a direction parallel to the planes of the first and second sheets; characterised in folding at least some of the microneedles out of the plane of the first or second sheet about a fold axis that extends parallel to the direction of relative displacement between the first and second arrays of microneedles.

Preferably, the method comprises locating each fold axis to lie in the plane of the first or second sheet.

Preferably, the method comprises the step of forming the first and/or second array of microneedles by stamping, punching, etching or laser cutting.

Preferably, the method comprises the step of at least partially forming each opening in the first sheet by folding a respective microneedle out of the first sheet to at least partially define the opening.

Preferably, the method comprises forming the microneedles within the first and second sheets with a shape and orientation such that when folded out of the plane of the respective sheet a longitudinal axis of each of the microneedles extend at an oblique angle to the plane of the first or second sheet.

Preferably, the method comprises orienting the first sheet relative to the second sheet such that a longitudinal axis of each of the microneedles of the first array extend in a first direction and a longitudinal axis of each of the microneedles of the second array extend in a second direction.

Preferably, the method comprising securing the first and second sheets in face to face engagement while permitting the relative displacement therebetween.

Preferably, the method comprises forming the microneedles within the first and second sheets to be substantially planar and folding the microneedles to lie in a plane perpendicular to the plane of the first and second sheet and parallel to the direction of relative displacement between the first and second sheets.

Preferably, the method comprises the step of forming a taper in a tip of each of the microneedles.

Preferably, the method comprises the step of forming multiple tapers in the tip.

Preferably, the method comprises the step of forming a multifaceted tip.

Preferably, the method comprises applying a coating to one or more of the microneedles.

Preferably, the method comprises the step of forming at least one tab in the first or second sheet adapted to engage a respective first or second microneedle once folded out of the plane of the first or second sheet in order to retain the microneedle at a desired orientation relative to the sheet.

BRIEF DESCRIPTION OF THE DRAWINGS

The present invention will now be described with reference to the accompanying drawings, in which.

DETAILED DESCRIPTION OF THE DRAWINGS

Figure 2:
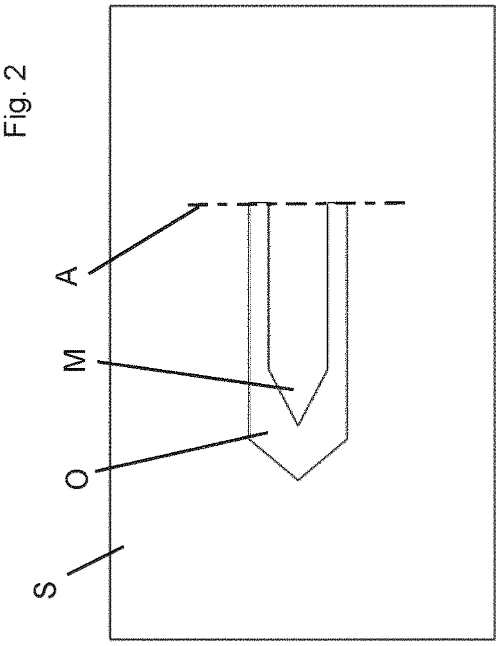
FIG. 2 illustrates an enlarged plan view of a single microneedle from the array illustrated in FIG. 1.
Figure 3:
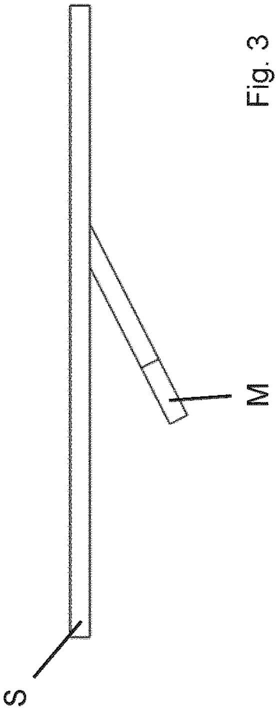
FIG. 3 illustrates an enlarged side elevation of the single microneedle as illustrated in FIG. 2.
Figure 1:
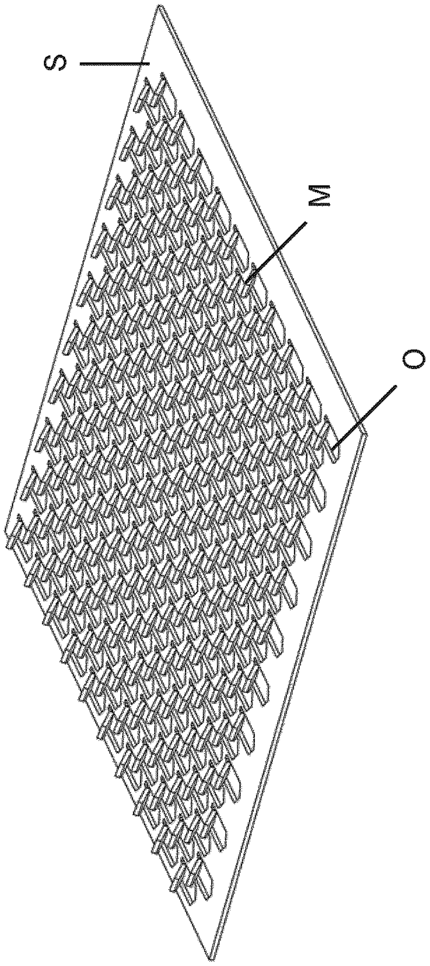
FIG. 1 illustrates a perspective view of a prior art array of microneedles stamped from and folded out of a sheet of metal.

Referring to FIGS. 1 to 3 of the accompanying drawings there is illustrated a known array of microneedles M formed integrally with a sheet S according to a known method of manufacture. The method of manufacture involves cutting or stamping out an array of openings O in the sheet S, preferably in a single stamping operation, to form the outline of each of the microneedles M in the 40 array. The method of manufacture utilises a conventional press (not shown) or the like to stamp out the openings O, and for example from a sheet of metal such as steel or titanium, although other materials may be employed.

FIGS. 2 and 3 show one of the microneedles M and surrounding opening O in isolation from the array, and enlarged, for illustrative purposes. Once the outlines of the microneedles M have been formed by stamping out the openings O, a further step in the manufacturing process involves bending or folding the microneedles M out of the plane of the sheet S, which again is undertaken using a conventional punch assembly. It can be seen that the microneedles M are bent about an axis A that extends transversely to the direction in which the microneedles M are displaced during insertion into tissue.

Turning then to FIGS. 4 to 17 there is illustrated a microneedle system generally indicated as 10, and a method of manufacturing the microneedle system 10, according to the present invention. The microneedle system 10 comprises an array of first microneedles 12 formed integrally with a first sheet 14 as hereinafter described, and a cooperating array of second microneedles 16 formed integrally with a second sheet 18, again as hereinafter described. As will be described in greater detail, the first and second sheets 14, 18 are located, in use, in face to face engagement such that the second microneedles 16 project through the first sheet 14 to be interspersed with the first microneedles 12, preferably in cooperating pairs of first and second microneedles 12, 16. The first and second microneedles 12, 16 are displaceable relative to one another in a longitudinal or "X" direction in order to transition the system 10 between a disengaged and an engaged state for penetrating and therefore anchoring to tissue (not shown). The underlying methodology of this deployment technique is described in detail in the above mentioned international applications WO2018/069543 and WO2019/201903. For ease of reference, hereinafter directions or dimensions along the length of the device 10 and sheets 14, 18 will be referred to as being an "X" coordinate or direction, along the width will be referred to as being a 'Y'" coordinate and along the depth will be referred to as being a "Z" coordinate, and as represented graphically in FIG. 9 relative to the microneedle system 10.

Figure 5:
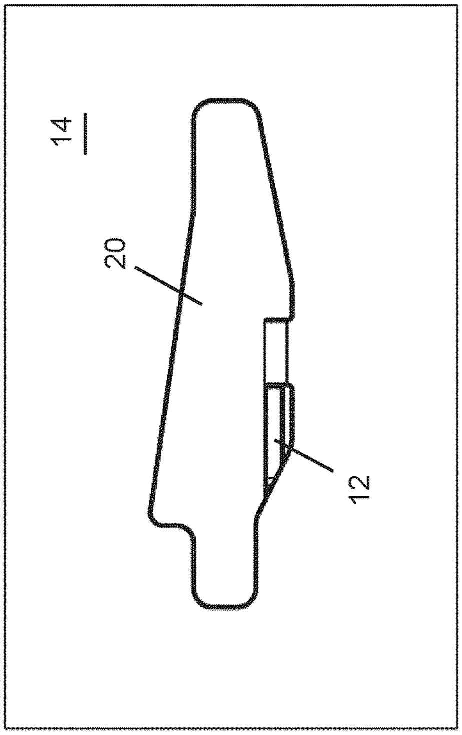
FIG. 5 illustrates the arrangement of FIG. 4 in which the first microneedle has been folded down out of the plane of the first sheet about a fold axis.
Figure 4:
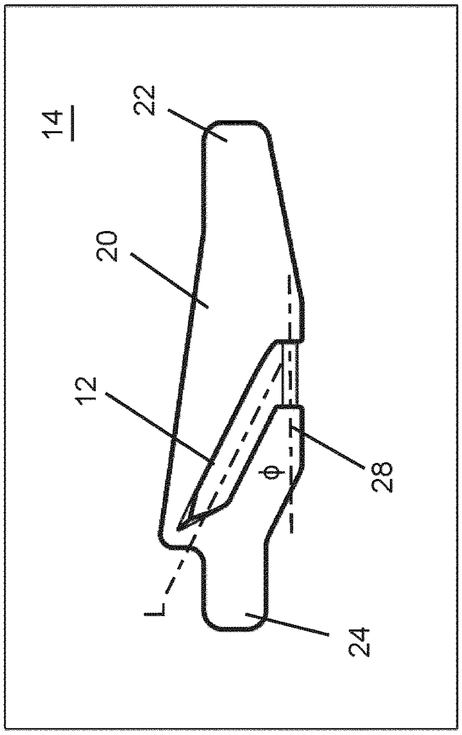
FIG. 4 illustrates a plan view of part of a first sheet in which a profile or outline of a first microneedle has been cut or otherwise formed, with additional material removed to form a profiled aperture surrounding the microneedle outline.
Figure 7:
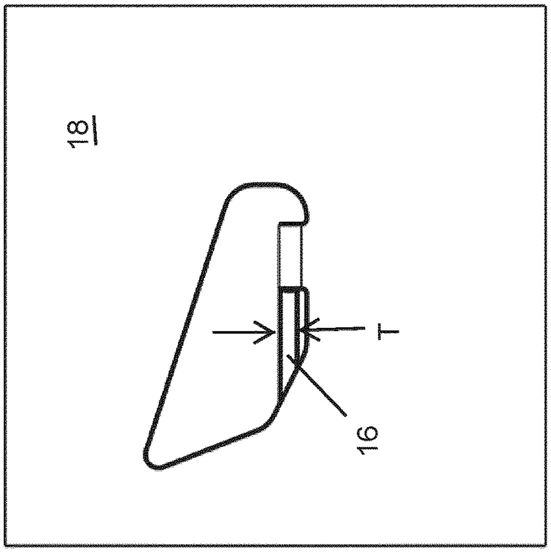
FIG. 7 illustrates the arrangement of FIG. 6 in which the second microneedle has been folded down out of the plane of the second sheet about a fold axis.
Figure 6:
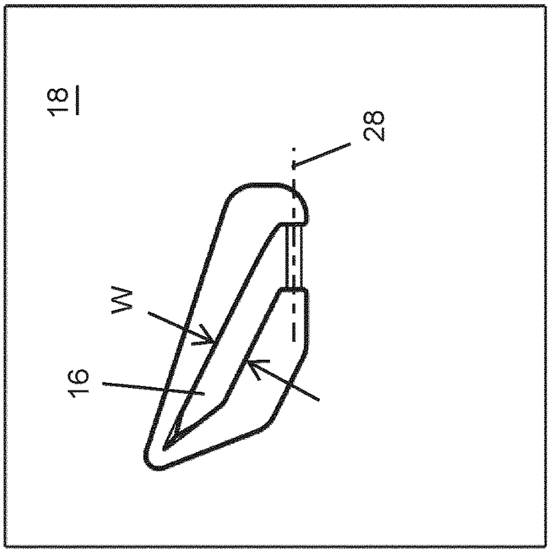
FIG. 6 illustrates a plan view of part of a second sheet in which a profile or outline of a second microneedle has been cut or otherwise formed in the second sheet.

In the drawings the complete first sheet 14 and/or second sheet 18 are shown only in FIGS. 14 to 17, while FIGS. 4 to 13 show a portion of each sheet 14, 18 containing a respective single microneedle 12, 16 in order to provide a clear view of the local arrangement and interaction of one cooperating pair of the microneedles, 12, 16. It will be understood that this arrangement and interaction as described hereinafter is repeated throughout the array for each cooperating pair of microneedles 12, 16. The microneedles 12, 16 are formed integrally with the respective sheet 14, 18 though a process of removing material from the sheet 14, 18 to define a profile or outline of the microneedle 12, 16 as illustrated in FIGS. 4 and 6, and then a subsequent step of folding the microneedle 12, 16 out of the plane of the sheet 14, 18 as illustrated in FIGS. 5 and 7. The material from around each microneedle 12, 16 may be removed by any suitable process, for example stamping, chemical etching, laser cutting, or any other functional alternative. The final shape of the microneedles 12, 16 may be varied and may have different geometries to suit a particular application or manufacturing process. In the embodiment illustrated both microneedles 12, 16 have a similar geometry, being elongate along a longitudinal axis L relative to a width W transverse to the longitudinal axis L, and having a thickness T equal to the thickness of the sheet 14, 18. It will however be appreciated that the thickness T could be modified through additional manufacturing steps, for example being reduced in thickness along the whole or part of the length of the microneedle 12, 16, or increased in thickness, for example by the application of one or more coatings or material through some other additive manufacturing process. It is however preferable for manufacturing efficiency that the final shape of the microneedles 12, 16 can be stamped or otherwise cut from the sheet 14, 18 in a single step. Additionally or alternatively at least a part of one or more of the microneedles 12, 16 may be provided with a coating such as an electrically isolating or insulating coating (not shown) and/or a pharmacologically active substance or composition. In the case of an electrically isolating or insulating coating, it would be possible for example to coat a substantial length of the microneedle(s) 12, 16 but leave a portion uncoated such as the tip, which would then allow the microneedles 12, 16 to be used to measure skin impedance at specific depths.

The sheets 14, 18 may be formed from any suitable material, for example metal or an alloy of metals, plastic or composite, or any suitable combination of materials, and may be of any suitable thickness and surface area, for example large sheets may be processed to form the microneedles 12, 16 and the sheets may then be divided into multiple smaller sections to produce the final working article.

Figure 9:
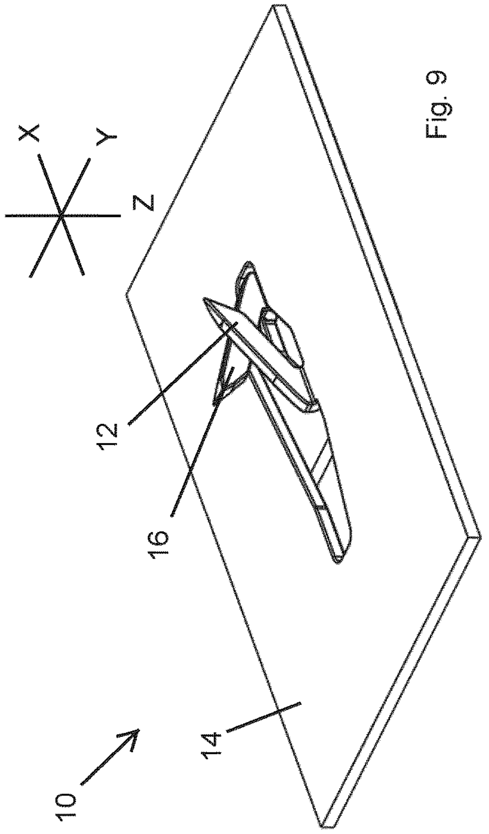
FIG. 9 illustrates the first and second sheet parts shown in FIG. 8 brought together into co-operating engagement with one another such that the second microneedle projects through an opening in the first sheet, and with the first and second microneedles in an disengaged state.
Figure 10:
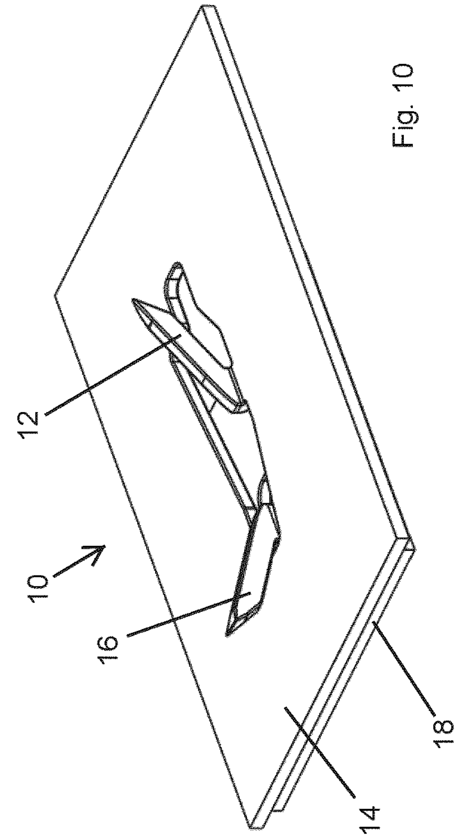
FIG. 10 illustrates the arrangement of FIG. 9 with the first and second microneedles in an engaged state.
Figure 8:
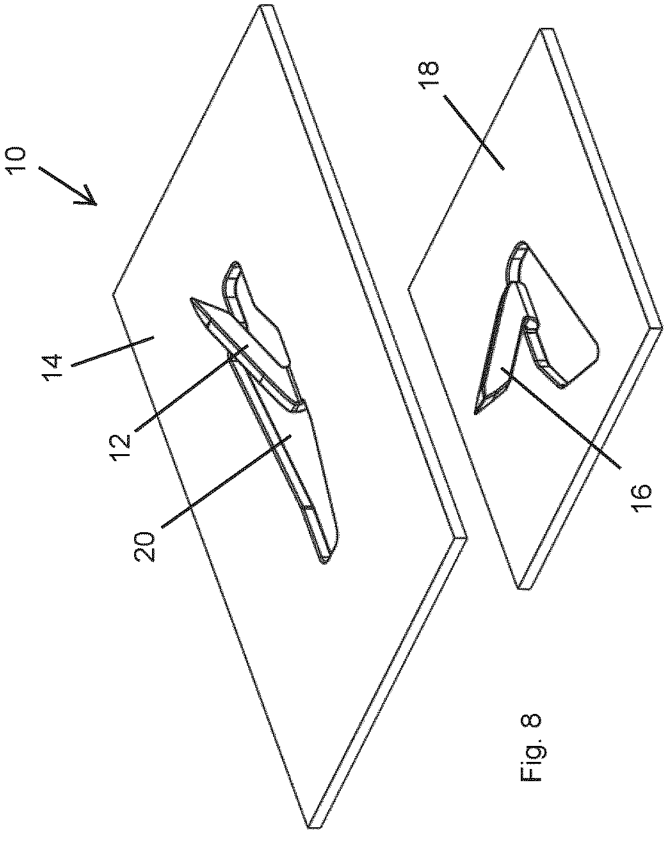
FIG. 8 illustrates a perspective view of the part of the first and second sheet as shown in FIGS. 5 and 7, overlying but separated vertically from one another for illustrative purposes, and for use in a microneedle system according to the present invention.
Figure 11:
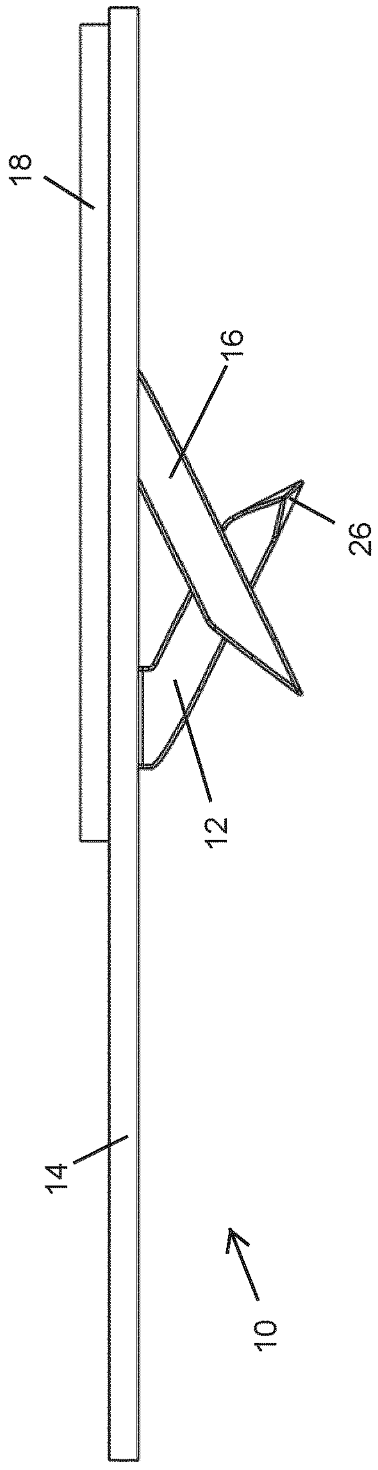
FIG. 11 illustrates a side elevation of the arrangement of FIG. 9.
Figure 12:
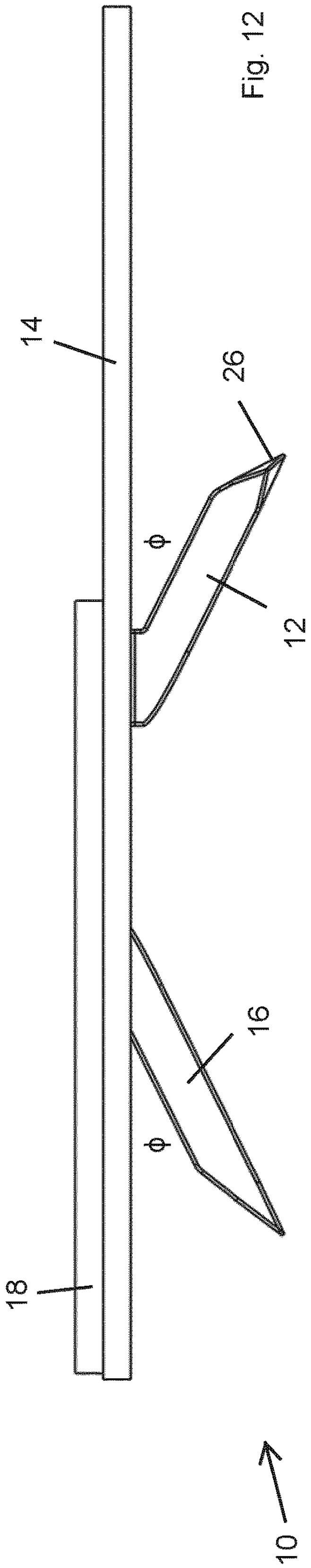
FIG. 12 illustrates a side elevation of the arrangement of FIG. 10.

It will be appreciated that once the microneedles 12, 16 are folded out of the sheet 14, 18 a hole approximately in the form of a negative of the microneedle 12, 16 will be left in the sheet 14, 18. However in forming the outline of each of the first microneedles 12 additional material is also removed to define a longitudinally elongate opening 20, which is preferably fully formed in the same step as stamping or otherwise forming the outline of the first microneedles 12. The opening 20 is arranged to allow the cooperating second microneedle 16 to pass through the first sheet 14 in the "Z" direction when the first and second sheets 14, 18 are located in face to face engagement, and to therefore be located in adjacent alignment with a paired one of the first microneedles 12 as can be seen in FIGS. 9 and 10. The opening 20 comprises the area resulting from removal of the respective first microneedle 12, in addition to a longitudinally extended first end 22 and opposed longitudinally extending second end 24. These ends 22, 24 permit longitudinal or "X" direction displacement of the second microneedle 16 relative to the first microneedle 12 as the system 10 is transitioned between the disengaged and engaged states as mentioned above. This is achieved through relative displacement of the first and second sheets 14, 18 longitudinally or in the "X" direction. The sheets 14, 18 effectively slide over one another along a limited path or distance, which in the present embodiment is effectively the distance the second microneedle 16 is displaceable from a position located in the first end 22 to a position located in the second end 24 of the opening 20, again as represented in FIGS. 9 and 10 respectively. This distance can of course be varied as required, most readily by increasing the overall longitudinal or "X" dimension of the opening 20. Thus the geometry of the opening 20 can be used to dictate the range of relative displacement between the microneedles 12, 16.

If required a suitable bearing (not shown) may be provided in the device 10 to facilitate the relative displacement between the sheets 14, 18. This may for example take the form of a low friction coating or component (not shown) located between the sheets 14, 18 or on one face of one of the sheets 14, 18. However given the small relative displacement between the sheets 14, 18, and that most applications of the system 10 are singe use, such a bearing (not shown) is unlikely to be a requirement to ensure effective operation of the system 10. Alternatively, the coating could be of an appropriate formulation to electrically-isolate each of the sheets 14, 18 of microneedle arrays from one another. This would facilitate the direct measurement of skin impedance using the microneedles 12, 16 as detailed above.

Turning then to the specific design of the microneedles 12, 16, it can be seen that the longitudinal axis L of each microneedle 12, 16 extends at an oblique angle $\phi$ to the plane of the sheets 14, 18, namely the "XY" plane, which angle $\phi$ may be varied as required, for example to be application specific. The first microneedles 12 are oriented to extend in a first direction while the second microneedles 16 extend in a second effectively opposite direction. In the embodiment illustrated the microneedles 12, 16 are arranged, with the system 10 in the disengaged state, to overlap in the longitudinal or "X" direction as most clearly visible in FIG. 11, but which can also be seen in FIG. 9. By longitudinally displacing the sheets 14, 18 relative to one another the system 10 is transitioned into the engaged state with the microneedles 12, 16 also displaced longitudinally relative to one another into the orientation shown in FIGS. 10 and 12.

It this position the microneedles 12, 16 have effectively moved past and are separated from one another longitudinally, with no overlap in the "X" direction. It should however be understood that the microneedle system 10 may be modified to employ alternative disengaged and engaged relative orientations, for example with variation in the longitudinal overlap between the microneedles 12, 16. This intentional "X" direction overlap improves manufacturability, by preventing tangling or interference of the microneedles 12, 16 during the overlying process and initial sliding process. Appreciably, when folding metal at this scale there can be substantial spring-back that is difficult to control for (particularly with certain materials, for example stainless steel), so the overlap reduces the requirement to have the microneedles 12, 16 folded to be exactly perpendicular to the plane of the first or second sheets 14, 18.

The length of the microneedles 12, 16 along the longitudinal axis L may also be varied as required. It can also be seen from FIG. 13 that in the "Y" direction the microneedles 12, 16 are laterally separated from one another in order to avoid contact as the microneedles 12, 16 move relative to one another in the "X" direction.

It can also be seen, in particular from FIGS. 11 to 14, that with the sheets 14, 18 in interlocking engagement the microneedles 12, 16 extend to the same depth ("Z" direction) and it will therefore be appreciated that the second microneedles 16 will preferably have a greater "Z" dimension than the first microneedles 12, and in particular an increased "Z" dimension equivalent to the thickness of the first sheet 14 through which the second microneedles 16 project. In this way the microneedles 12, 16 will both extend to the same depth in the "Z" direction, although is also envisaged that the microneedles may extend to different depths, or that certain pairs of microneedles 12, 16 within the fuller array may be so configured. It is also intended, in the machining and creation of the apertures in the first and second sheets 14, 18 to define the microneedles 12, 16, to optionally create geometries (tabs, etc.—not shown) which effectively engage with one another to click-lock the individual needles 12, 16 into the perpendicular orientation.

The microneedles 12, 16 preferably include a tapered tip 26 to improve tissue penetration. The tip 26 may be tapered or faceted in multiple directions/planes. This tapering or faceting is preferably formed prior to folding the microneedles 12, 16 out of the sheets 14, 18, although could be applied afterwards. The tip 26 or some or all the microneedles 12, 16 may be provided with a coating (not shown) to modify the physical properties of the microneedles 12, 16, for example a coating to harden the tip 26. This coating may be applied by any suitable method, for example vapour deposition. Additionally or alternatively the tip 26 and/or microneedle 12, 16 may be coated in a pharmacologically active compound or drug to be delivered when the system 10 is deployed in tissue. As an alternative the microneedles 12, 16 may be hollow and the system 10 may be adapted to effect drug delivery from or through the hollow microneedles.

Figure 13:
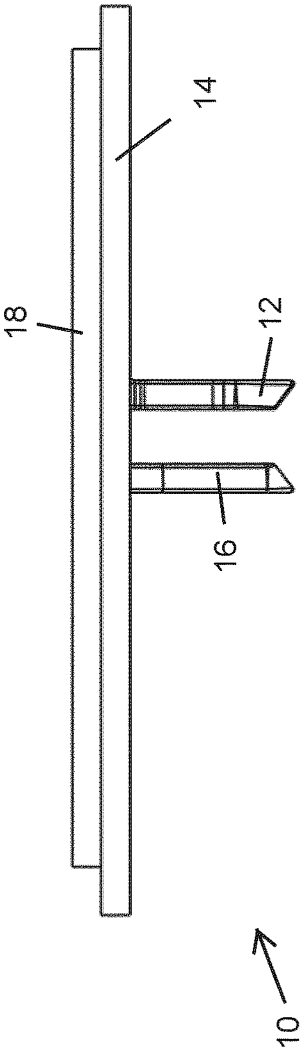
FIG. 13 illustrates an end elevation of the arrangement of FIG. 9 or 10.
Figure 15:
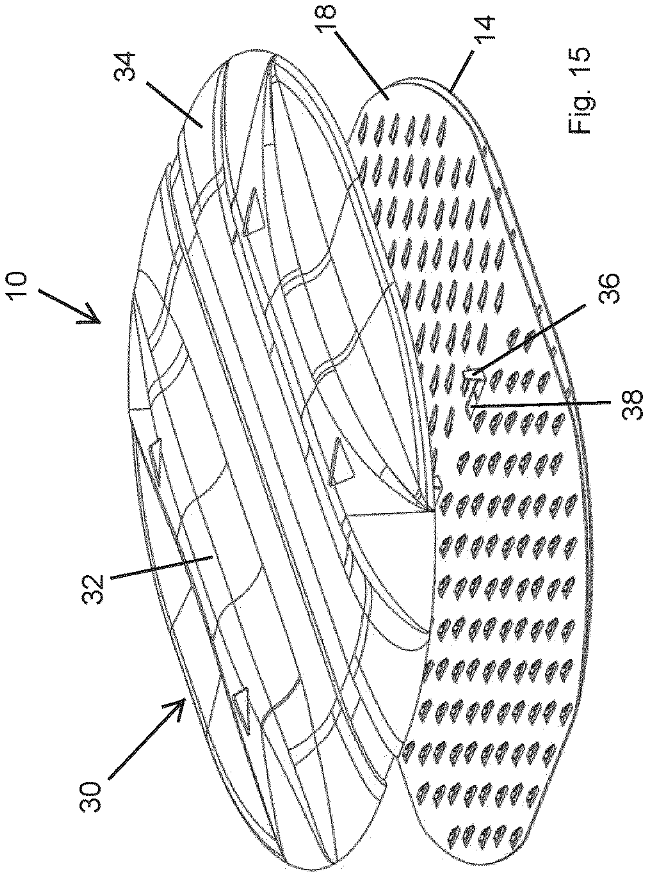
FIG. 15 illustrates the skin patch of FIG. 14 with the first and second array of microneedles brought together into co-operating engagement with one another.
Figure 17:
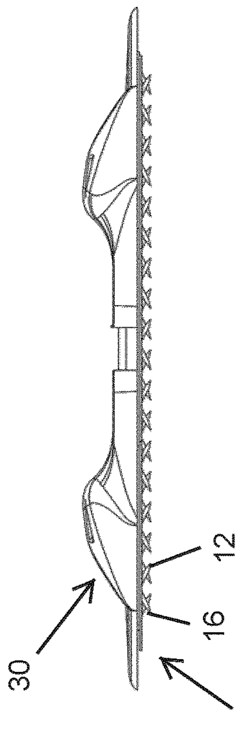
FIG. 17 illustrates a side elevation of the skin patch shown in FIG. 16.
Figure 14:
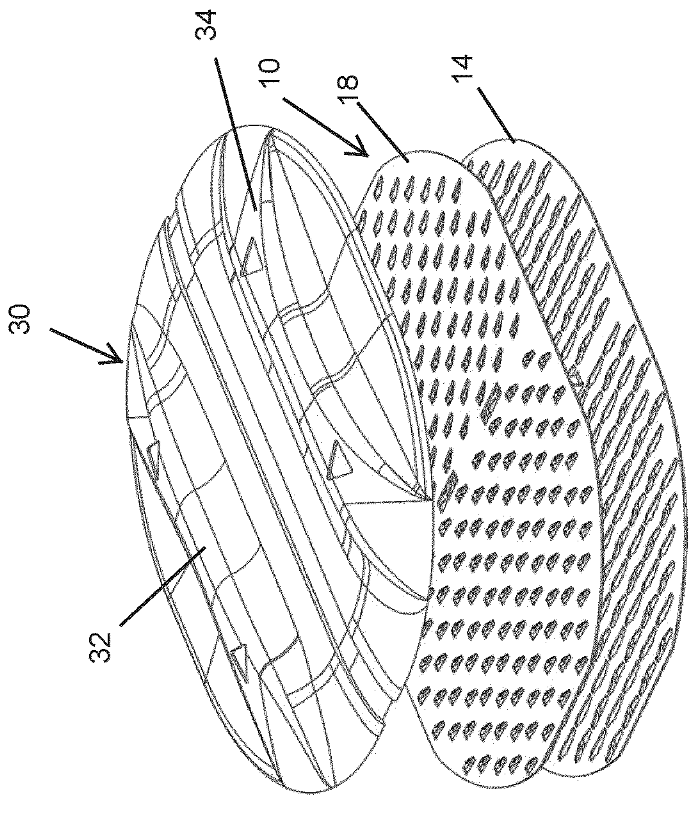
FIG. 14 illustrates an exploded perspective view of a microneedle based skin patch containing a first and second array of microneedles shown separated from one another.
Figure 16:
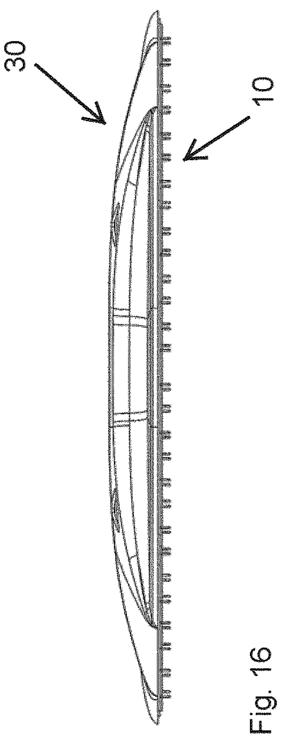
FIG. 16 illustrates a side elevation of the skin patch shown in FIGS. 14 and 15.

Referring in particular to FIGS. 4 to 10 it is seen that that the microneedles 12, 16 are folded out of the "XY" plane of the sheet 14, 18 along a fold axis 28 that extends in the longitudinal or "X" direction. This has a number of benefits, notably a significant increase in the strength of the microneedles 12, 16 in resisting longitudinal loading during tissue insertion, and the ability to significantly increase the density of the microneedles 12, 16 on a given area of sheet 14, 18. Thus when forming the outline of the microneedles 12, 16, as shown in FIGS. 4 and 6, the microneedles 12, 16 are arranged to extend at the oblique angle $\phi$ to the longitudinal or "X" direction so that, once folded out of the "XY" plane of the sheet 14, 18 the microneedles 12, 16 will be oriented at the oblique angle $\phi$ to the "XY" plane of the sheet 14, 18. The angle $\phi$ is thus defined between the fold axis 28 and the longitudinal axis L of the microneedles 12, 16. FIG. 13 further illustrates that the microneedles 12, 16 preferably extend, in the "Z" direction, at an orientation perpendicular to the "XY" plane of the sheets 14, 18, although the orientation may be varied. By arranging the fold axis 28 in line with the direction of relative displacement between the microneedles 12, 16 the cooperating pairs of microneedles 12, 16, once folded out of the sheet 14, 18, are oriented to have their smallest dimension, the thickness T, side by side as can be seen most clearly in FIG. 13. This orientation of the microneedles 12, 16 significantly increases the density of the cooperating microneedles 12, 16 that can be arranged in a given area of the sheets 14, 18, in particular relative to the prior art orientation as illustrated in FIG. 1. This increased density can provide increased adherence to tissue and/or increased drug delivery capacity.

Referring to FIGS. 14 to 17 the microneedle system 10 is shown comprising an exemplary manual applicator 30 which is operable to effect relative displacement of the sheets 14, 18 in order to transition the system 10 between the disengaged and engaged states. The configuration and operation of this form of applicator 30 is described and shown in detail in the Applicant's co-pending European patent application no. 20198798.9. The applicator 30 comprises a pair of halves 32, 34 which may be displaced relative to one another, and to the underside of which the pair of sheets 14, 18 may be secured, releasably or permanently. A pair of tabs 36 is provided on the first sheet 14 and project through a corresponding pair of apertures 38 in the second sheet 18 which are dimensioned to permit the longitudinal relative displacement of the tabs 36 in order to effect the relative displacement of the sheets 14, 18. The tabs 36 are secured to the underside of the applicator 30 and displacement of the pair of halves 32, 34 is arranged to effect displacement of the tabs 36 along the apertures 38 and therefore to effect relative displacement of the sheets 14, 18 and consequently the microneedles 12, 16. In this way the system 10 may be pressed into contact with tissue such as the skin (not shown), and the pair of halves 32, 34 manually pressed together to deploy the microneedles 12, 16 into the skin. The applicator 30 may then be removed to leave the sheets 14, 18 applied to the skin, or the applicator 30 may remain in place to permit the subsequent removal of the sheets 14, 18 by reversing the above procedure to retract the microneedles 12, 16 from the skin or other tissue.

Figure 18:
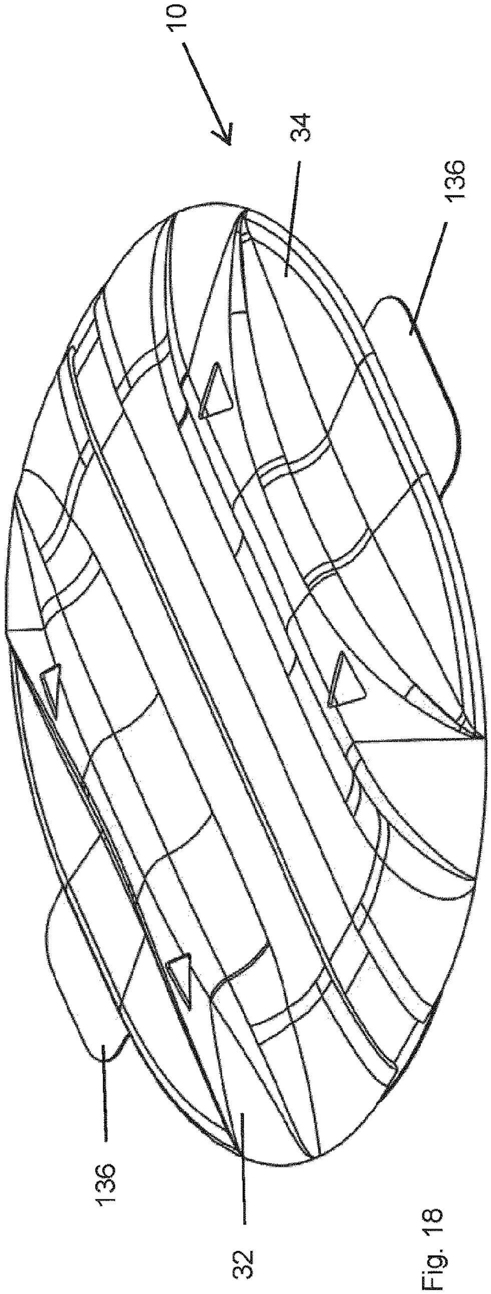
FIG. 18 illustrates the skin patch of FIGS. 14 to 17 with modified retention tabs in an open state.
Figure 19:
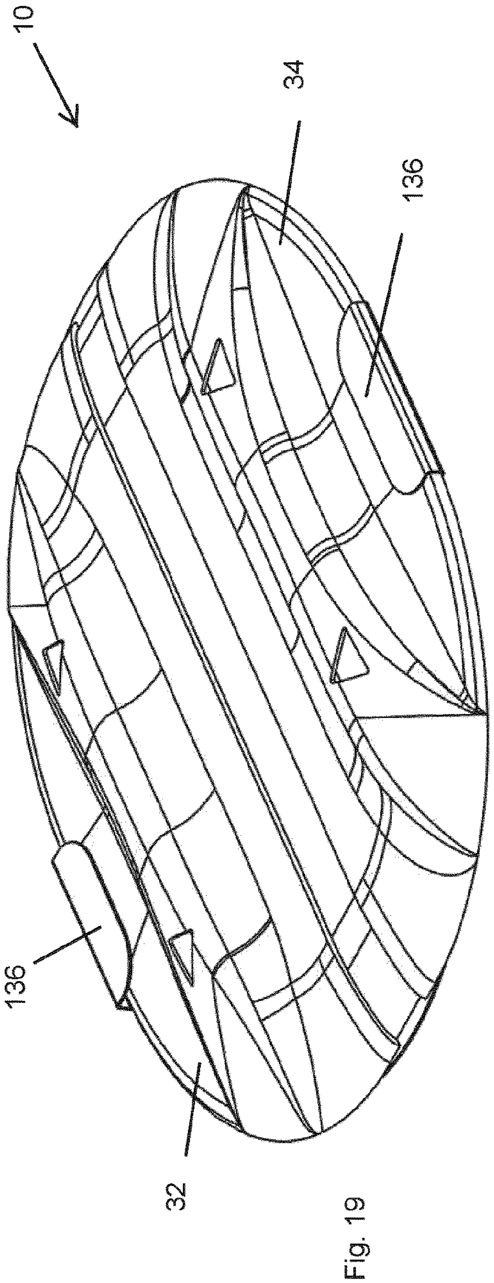
FIG. 19 illustrates the skin patch as shown in FIG. 18 with the retention tabs in a closed state.

FIGS. 18 and 19 illustrate the microneedle system 10 as shown in FIGS. 14 to 17 in which each of the pair of sheets (not visible) of microneedles is modified to be provided with a retention tab 136 extending laterally from one edge thereof and thus extending beyond the edge of the respective half 32, 34 of the applicator 30. Each of the retention tabs 136 is displaceable from an open position as illustrated in FIG. 18 to be folded around the edge of the respective half 32, 34 to overlie same and thus secure the respective sheet of microneedles to the respective half 32, 34 of the applicator. The retention tabs 138 may be used in place of or in combination with the pair of tabs 36 shown in FIG. 15. The tabs 138 may be elastically deformable or otherwise reversibly displaceable between the open and closed positions. In this way, once the sheets have been deployed onto the skin the retention tabs 138 may be returned to the open state to allow the applicator 30 to be removed such as to leave only the sheets of microneedles on the skin.

It will be appreciated that the applicator 30 based microneedle system 10 is merely an exemplary application of the microneedle system 10, the essential components of which are the pair of sheets 14, 18 carrying the array of cooperating microneedles 12, 16. These sheets 14, 18 may be incorporated into any other suitable medical or surgical device to permit deployment into tissue, whether externally as with skin or ocular applications, biosensing applications, drug delivery or anchorage of other medical equipment or the like, or internally for surgical or drug delivery applications.

It will therefore be appreciated that the system 10 and method of manufacture according to the present invention provides microneedle arrays which are of a configuration which increases the strength of the microneedles during tissue penetration, increases the density of the microneedles for a given surface area of sheet on which the microneedles are formed, and facilitates the high volume manufacture of such microneedle arrays.

The invention is not limited to the embodiment described herein but can be amended or modified without departing from the scope of the present invention.

The invention claimed is:

1. A microneedle system for application to tissue comprising a first array of microneedles formed from and folded out of a plane of a first sheet; a second array of microneedles formed from and folded out of a plane of a second sheet; the first and second sheets overlie one another and the second array of microneedles extends through an array of openings in the first sheet to be interspersed with the first array of microneedles; wherein the first array of microneedles is displaceable relative to the second array of microneedles in a direction parallel to the plane of the first and second sheets; characterized in that at least some of the microneedles are folded out of the plane of the first or second sheet about a fold axis that extends parallel to the direction of relative displacement between the first and second arrays of microneedles.

2. The microneedle system of claim 1 in which the fold axis lies in the plane of the first or second sheet.

3. The microneedle system of claim 1 in which the openings in the first sheet are shaped and dimensioned to facilitate the relative movement between the first and second arrays of microneedles.

4. The microneedle system of claim 1 in which the openings in the first sheet are at least partially formed by folding a respective microneedle out of the first sheet to at least partially define the opening.

5. The microneedle system of claim 1 in which a longitudinal axis of each of the microneedles in the first and second arrays extend at an oblique angle to the plane of the first or second sheet.

6. The microneedle system of claim 1 in which a longitudinal axis of each of the microneedles of the first array extend in a first direction and a longitudinal axis of each of the microneedles of the second array extend in a second direction.

7. The microneedle system of claim 6 in which the first direction extends away from the second direction.

8. The microneedle system of claim 6 in which the longitudinal axis of each of the microneedles of the first array extend at a first oblique angle to the plane of the first and second sheet and the longitudinal axis of each of the microneedles of the second array extend at a second oblique angle to the plane of the first and second sheet.

9. The microneedle system of claim 1 in which each of the microneedles of the first and second arrays comprises a tapered tip.

10. The microneedle system of claim 1 in which the tip is tapered in multiple directions.

11. The microneedle system of claim 9 in which the tip is multifaceted.

12. The microneedle system of claim 1 in which the first and second sheets comprise metal.

13. The microneedle system of claim 1 in which at least a part of one or more of the microneedles comprise an exterior coating.

14. The microneedle system of claim 13 in which the coating comprises a pharmacologically active component and/or an electrically insulating material.

15. The microneedle system of claim 1 in which the first sheet is electrically isolated from the second sheet.

16. A method of manufacturing a microneedle system comprising the steps of forming a first array of microneedles in a first sheet; folding the first microneedles out of a plane of the first sheet; forming a second array of microneedles in a second sheet; folding the second microneedles out of a plane of the second sheet; overlying the first and second sheets such that the second array of microneedles extends through an array of openings in the first sheet to be interspersed with and displaceable relative to the first array of microneedles in a direction parallel to the planes of the first and second sheets; characterized in folding at least some of the microneedles out of the plane of the first or second sheet about a fold axis that extends parallel to the direction of relative displacement between the first and second arrays of microneedles.

17. The method of manufacturing a microneedle system of claim 16 comprising locating each fold axis to lie in the plane of the first or second sheet.

18. The method of manufacturing a microneedle system of claim 16 comprising the step of forming the first and/or second array of microneedles by stamping, punching, etching or laser cutting.

19. The method of manufacturing a microneedle system of claim 16 comprising the step of at least partially forming each opening in the first sheet by folding a respective microneedle out of the sheet to at least partially define the opening.

20. The method of manufacturing a microneedle system of claim 16 comprising forming the microneedles within the first and second sheets with a shape and orientation such that when folded out of the plane of the respective sheet a longitudinal axis of each of the microneedles extend at an oblique angle to the plane of the first or second sheet.

21. The method of manufacturing a microneedle system of claim 16 comprising orienting the first sheet relative to the second sheet such that a longitudinal axis of each of the microneedles of the first array extend in a first direction and a longitudinal axis of each of the microneedles of the second array extend in a second direction.

22. The method of manufacturing a microneedle system of claim 16 comprising securing the first and second sheets in face to face engagement while permitting the relative displacement therebetween.

23. The method of manufacturing a microneedle system of claim 16 comprising forming a taper in a tip of each of the microneedles.

24. The method of manufacturing a microneedle system of claim 16 comprising applying a coating to one or more of the microneedles.

25. The method of manufacturing a microneedle system of claim 16 comprising the step of forming at least one tab in the first or second sheet adapted to engage a respective first or second microneedle once folded out of the plane of the first or second sheet in order to retain the microneedle at a desired orientation relative to the sheet.

* * * * *